United States Patent
Atallah et al.

(10) Patent No.: US 11,559,616 B2
(45) Date of Patent: Jan. 24, 2023

(54) METHOD AND SYSTEM FOR POSTDIALYTIC DETERMINATION OF DRY WEIGHT

(71) Applicant: B. BRAUN AVITUM AG, Melsungen (DE)

(72) Inventors: Richard Atallah, Kassel (DE); Florian Bauer, Lindlar (DE)

(73) Assignee: B. Braun Avitum AG, Melsungen (DE)

( * ) Notice: Subject to any disclaimer, the term of this patent is extended or adjusted under 35 U.S.C. 154(b) by 954 days.

(21) Appl. No.: 15/679,656

(22) Filed: Aug. 17, 2017

(65) Prior Publication Data

US 2018/0050144 A1    Feb. 22, 2018

(30) Foreign Application Priority Data

Aug. 22, 2016  (DE) ..................... 10 2016 115 496.2

(51) Int. Cl.
*A61M 1/16* (2006.01)
*A61M 1/34* (2006.01)
(Continued)

(52) U.S. Cl.
CPC .......... *A61M 1/1611* (2014.02); *A61B 5/4875* (2013.01); *A61B 5/7267* (2013.01); *A61B 6/50* (2013.01); *A61M 1/16* (2013.01); *A61M 1/1601* (2014.02); *A61M 1/1613* (2014.02); *A61M 1/34* (2013.01); *A61M 1/3413* (2013.01);
(Continued)

(58) Field of Classification Search
CPC .............. A61M 1/1611; A61M 1/1601; A61M 1/1613; A61M 1/16; A61M 1/34; A61M 1/3413; G16H 20/17; G16H 50/20; A61B 5/4875; A61B 5/7267; A61B 6/50; G06N 3/02
See application file for complete search history.

(56) References Cited

U.S. PATENT DOCUMENTS 8,496,807 B2  7/2013  Mori et al.
8,568,595 B2  10/2013  Castellarnau
(Continued)

FOREIGN PATENT DOCUMENTS

CN  101193667 A  6/2008
CN  101304773 B  11/2008
(Continued)

OTHER PUBLICATIONS

European search report for European Application No. 17186368.1, dated Jan. 17, 2018 with translation, 14 pages.
(Continued)

*Primary Examiner* — Daniel L Cerioni

(74) *Attorney, Agent, or Firm* — Christopher A. Rothe; Culhane Meadows, PLLC

(57) ABSTRACT

A method for determining the dry weight of a patient after dialysis therapy, wherein the patient's blood volume is monitored and blood volume values are output. The blood volume values are recorded and evaluated for a predetermined period of time after reaching an ultrafiltration volume appropriately predetermined for the patient, wherein the dry (Continued)

weight of the patient then is determined on the basis of the rate of change of the blood volume during the predetermined period of time.

10 Claims, 3 Drawing Sheets

(51) Int. Cl.
*A61B 5/00* (2006.01)
*G16H 50/20* (2018.01)
*G16H 20/17* (2018.01)
*A61B 6/00* (2006.01)
*G06N 3/02* (2006.01)
*A61B 5/145* (2006.01)

(52) U.S. Cl.
CPC .............. *G06N 3/02* (2013.01); *G16H 20/17* (2018.01); *G16H 50/20* (2018.01); *A61B 5/145* (2013.01); *A61M 2205/52* (2013.01); *A61M 2230/207* (2013.01)

(56) References Cited

U.S. PATENT DOCUMENTS

| | | | |
|---|---|---|---|
| 2003/0120170 A1 | 6/2003 | Zhu et al. | |
| 2005/0197982 A1* | 9/2005 | Saidi | G06N 3/084 706/21 |
| 2007/0108129 A1* | 5/2007 | Mori | A61M 1/361 210/646 |
| 2011/0089111 A1 | 4/2011 | Mori et al. | |
| 2013/0331712 A1* | 12/2013 | Moissl | A61B 5/4848 600/483 |
| 2014/0200181 A1* | 7/2014 | Fuertinger | G16H 50/20 514/7.7 |
| 2014/0249384 A1 | 9/2014 | Levin et al. | |
| 2014/0316292 A1* | 10/2014 | McRae | A61B 5/7275 600/504 |
| 2015/0045713 A1 | 2/2015 | Attalah et al. | |
| 2016/0058933 A1* | 3/2016 | Ballantyne | A61M 1/1656 210/85 |
| 2018/0050144 A1 | 2/2018 | Atallah et al. | |

FOREIGN PATENT DOCUMENTS

| | | |
|---|---|---|
| CN | 102159260 A | 8/2011 |
| CN | 209529783 U | 10/2019 |
| DE | 102013108543 A1 | 2/2015 |
| JP | 2002165876 A | 6/2002 |
| JP | 2014530669 A | 11/2014 |
| WO | 2013043598 A1 | 3/2013 |

OTHER PUBLICATIONS

German Search Report for German Application No. 10 2016 115 496.2, with partial translation, dated Apr. 3, 2017—17 Pages.

Lopot et al., "Continuous Blood Volume Monitoring and 'Dry Weight' Assessment", Journal of Renal Care, Apr. Jun. 2007, pp. 52-58.

Rodriguez et al., "Assessment of dry weight by monitoring changes in blood volume during hemodialysis using Crit-Line", Kidney International, vol. 68 (2005), pp. 854-861.

Chinese Examination Report received in Application No. 201710724814.3 dated Dec. 25, 2020, 31 pages.

Chinese Search Report received in Application No. 201710724814.3 dated Dec. 17, 2020, 6 pages.

Office Action received in Chinese Application No. 201710724814.3 dated Aug. 20, 2021, with translation, 12 pages.

Office Action received in Japanese Application No. 2017-157633 dated Aug. 3, 2021, with translation, 5 pages.

Search Report received in Chinese Application No. 201710724814.3 dated Aug. 11, 2021, with translation, 4 pages.

* cited by examiner

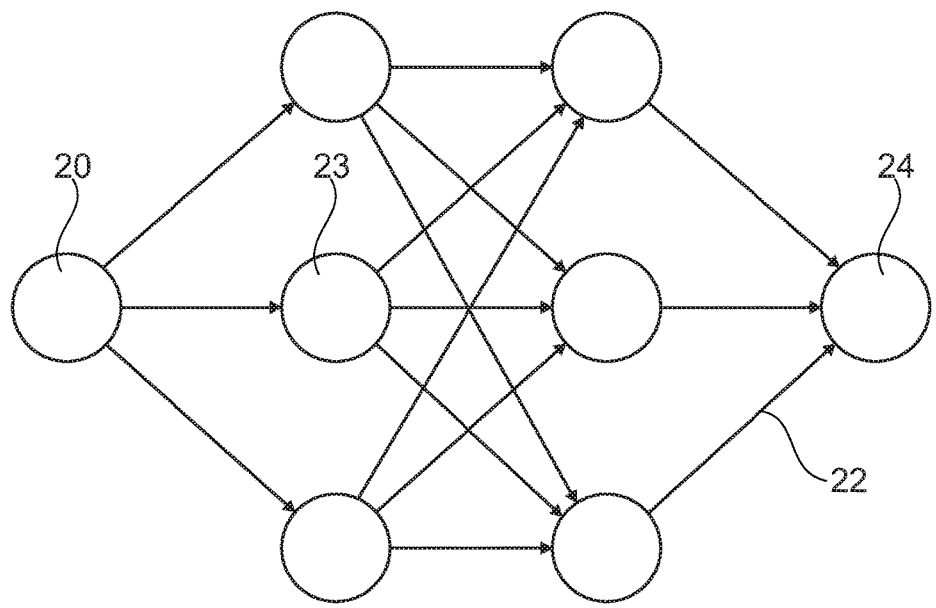

Fig. 2

| Training cycle/ Neuronal network | Neuronal network 1 | Neuronal network 2 | Neuronal network 3 | Neuronal network 4 | Neuronal network 5 | Neuronal network 6 |
|---|---|---|---|---|---|---|
| Input | Blood volume rebound | Blood volume rebound | Blood volume rebound | Blood volume rebound | Blood volume rebound | Blood volume rebound & last blood volume value |
| No. of hidden layers | 3 hidden layers (6,5,10 neurons) | 3 hidden layers (6,5,10 neurons) | 3 hidden layers L (4,10,10 neurons) | 3 hidden layers (7,10,9 neurons) | 3 hidden layers (3,10,5 neurons) | 3 hidden layers (4,8,10 neurons) |
| Performance (ml²) | 41,5 | 41,2 | 31,2 | 36,1 | 30,6 | 27,5 |

Fig. 3

| Training cycle/ Neuronal network | Neuronal network 1 | Neuronal network 2 | Neuronal network 3 | Neuronal network 4 | Neuronal network 5 | Neuronal network 6 |
|---|---|---|---|---|---|---|
| Input | Blood volume rebound | Blood volume rebound | Blood volume values of entire therapy | Blood volume rebound | Blood volume rebound | Blood volume rebound & last blood volume value |
| No. of hidden layers | 3 hidden layers (6,5,10 neurons) | 1 hidden layer (7 neurons) | 3 hidden layers (5,9,5 neurons) | 3 hidden layers (7,10,9 neurons) | 3 hidden layers (3,10,5 neurons) | 3 hidden layers (4,8,10 neurons) |
| Performance | 41,5 | 105,23 | 980 | 36,1 | 30,6 | 27,5 |

Fig. 4

METHOD AND SYSTEM FOR POSTDIALYTIC DETERMINATION OF DRY WEIGHT

CROSS REFERENCE TO RELATED APPLICATIONS

This application claims priority to German application DE 10 2016 115 496.2 filed Aug. 22, 2016, the contents of such application being incorporated by reference herein.

FIELD OF THE INVENTION

The present invention relates to a method and a system (and, respectively, an apparatus) for a measuring system for determining the dry weight of a patient in the dialysis routine. Especially, the invention relates to evaluating the dry weight obtained during dialysis therapy.

BACKGROUND OF THE INVENTION

It is the target of a dialysis therapy, apart from detoxication of the blood, to remove excess water that collects due to a renal failure underlying the dialysis in the body from the latter. This is done by so-called ultrafiltration in which fluid is removed from the blood via a dialyzer. During the so-called intradialytic period of time, 64% of water are depositing in the intracellular space, 28% of water are depositing in the interstice and only 8% of water are depositing in the blood.

When during ultrafiltration plasm is removed from the blood, water flows from the intracellular space into the intravascular space due to osmosis. This process is referred to as "refilling". It is the aim, inter alia, to remove the excess water from the body of a patient so as to get the patient to his/her initial weight without any hypervolemia and without any complications. This initial weight is also referred to as dry weight. Erroneous determination of the dry weight may result in major complications. For example, dry weight which is determined to be too low leads to high dehydration and thus to hypovolemia which is connected to hypotonia, whereas dry weight determined to be too high leads to constant hypervolemia. Both hypervolemia and hypovolemia of a patient are linked with a high mortality rate.

The determination of dry weight in dialysis routine is usually based on experiences and routines of the hospital staff, wherein e.g. the courses of blood pressure and blood volume of the therapies are evaluated and, accordingly, adequate dry weight is determined.

STATE OF THE ART

In accordance with the state of the art, for determining or judging the dry weight the approaches of bioimpedance measurement, of blood volume monitoring, of vena-cava diameter measurement and of the biochemical markers are differentiated which shall be briefly explained in the following.

During bioimpedance measurement two electrodes are connected to the patient and therebetween a low current (1 mA) of different frequencies (1 kHz-1 MHz) is transmitted. Due to the nature of the cell membrane and the fluid in the tissue which is penetrated by higher frequencies only, the fluid in the intracellular and extracellular space can be very accurately determined based on the impedance measured. The method offers snap-shots of the water balance of the various reservoirs in a predialytic, intradialytic and postdialytic state. By way of said values fluid transitions and the postdialytic final stage which provides information about a possible hypervolemia or hypovolemia then can be determined.

In vena-cava diameter measurement the diameter of the lower vena cava is determined with ultrasound. Due to the fluid retention in the interdialytic period of time, the veins are more expanded than in normally hydrogenated persons. The determined diameter of the vein is then compared to particular reference values. E.g. a diameter of 11 $mm/m^2$ indicates hypervolemia, whereas a diameter of 8 $mm/m^2$ indicates hypovolemia.

During blood volume monitoring the hematocrit content (Hct content corresponding to the share of erythrocytes in the blood) of the blood is determined by which the water content in the blood can be traced back. A high Hct content/value related to a defined volume indicates a low fluid level. In contrast to this, a low Hct value indicates hypervolemia. The blood volume is continuously read out during a therapy by a Hct sensor, and by way of the curve forming in this way a statement can be made about the water balance of the patient. Thus, the course of the blood volume curve is largely dependent on the ratio of the ultrafiltration rate to the endogenous refilling. If high refilling and, accordingly, a flat blood volume curve are provided, a possible hypervolemia can be concluded. These data are used by physicians and staff members to make an assessment by way of empirical and routine values about reaching the dry weight.

In the method using biochemical markers for example a marker for the atrial natriuretic peptide (ANP) can be utilized. Depending on the variations of the transmural pressure (difference between internal and external pressure in blood vessels, for example), ANP is formed and released in the cell tissue. ANP plays a decisive role for the water-salt homeostasis and has a very low dialysis clearance (the renal clearance indicates the elimination ("clearing") of a substance from the blood plasm). For this reason, said marker offers a good possibility of determining the endogenous fluid balance before and after dialysis. It was found that the ANP concentration definitely varies during a dialysis therapy and shows good correlations with the blood pressure.

However, the afore-mentioned approaches have not or only partly become accepted in the dialysis routine, as they provide only clues for an assessment of the dry weight. Thus, the dry weight is usually continued to be determined with the empirical values of the dialysis staff only.

Furthermore, the afore-mentioned approaches are connected to the following drawbacks:

For measuring the bioimpedance specific electrodes and a bioimpedance instrument are required, which entails additional costs. Furthermore, fastening of the electrodes and evaluation of the results during and, respectively, after the therapy entail extra work for the staff members of the dialysis center. In addition, no exact statement is made about the precise quantity of hypervolemia and hypovolemia, but only about the water exchange between the reservoirs and the filling level thereof. Accordingly, a physician is required to interpret the results, even though so-called shift vectors may be of help in the evaluation.

In the vena cava diameter method, the vein diameter is determined only at particular points in time (e.g. before, during or after the therapy). Influencing factors such vasoconstriction or other diseases which have an impact on the diameter of the vein are not taken into account. Further, changes of the vein diameter among different patients may have strong variations. This method further requires an additional ultrasonic apparatus and an interpreting physician, which entails an increased employment and cost of staff.

Blood volume monitoring is no direct method of determining the dry weight. This method provides the physician only with a clue which is considered by the physician for his/her personal estimation. Although the system provides precise values about the water content which is currently and related to the start of therapy provided in the blood, no statement is made, however, either about possible hypervolemia or hypovolemia or about the water quantity in the other reservoirs. The physician in charge has to evaluate the blood volume values on his/her own and, based on his/her experience, has to decide whether the dry weight will be maintained or shall be modified in further therapies. Hence, this is sort of a trial-and-error method in which the physician considers the behavior of the blood volume and then takes decisions regarding the amount of ultrafiltration. For this reason, this method provides no exact information about a dry weight which is chosen to be too high or too low.

Finally, the method using the biochemical markers allows detecting hypervolemia after therapy. However, hypovolemia cannot be determined by this method. Furthermore, the result of hypervolemia depends on the cardiac function of the patient, as said function decisively influences the filling level and thus also the transmural pressure. Despite a good correlation of the marker concentration with the blood pressure, the results of this method are insecure measured by the current standards. It is another drawback that this method is very complicated and time-consuming for mass application, as laboratory analyses and additional equipment as well as staff members for operating said additional equipment are required.

SUMMARY OF THE INVENTION

An object underlying the present invention is, inter alia, to provide a system, an apparatus, and a method of determining dry weight of a patient with which automatic and automated evaluation/judgment of the dry weight and easy implementation in existing systems are possible.

This object is achieved by systems, methods, apparatus, computer programs, and computer control methods according to the claims.

Hence, according to aspects of the invention, the rate of change or increase of the so-called blood volume rebound is determined upon reaching a set/predetermined ultrafiltration volume and it is checked with the aid of the learning means (e.g. neuronal network) whether a dry weight predefined for a patient has been reached and, unless this is the case, in how far the ultrafiltration volume can be adapted. Thus, an automatic evaluation of the dry weight is following, in contrast to the conventional approaches for mathematic or measuring processes which still have to be assessed and interpreted by the staff members in charge. The suggested system/apparatus and method, respectively, for determining the dry weight thus can be easily implemented in already existing systems (if the conventional system includes blood volume monitoring) and trains itself in a fully automated manner by the learning means and, respectively, the learning step.

Furthermore, the system, the apparatus, and, respectively, the method can be adapted to individual patients and at the end of each therapy furnishes an explicit statement about reaching the dry weight as well as possible adaptations of the ultrafiltration volume.

Hence, advantageously an exact determination of the dry weight via the blood volume rebound with a learning means (e.g. neuronal network) can take place, wherein an easy implementation in existing systems is possible. The integrated learning means and, respectively, the integrated learning step allow for independent learning and independent optimizing of the dry weight determination. The latter can be fully automated and no additional measuring instruments are required, which thus does not entail any special expenditure for the patient and the staff members.

As a result, a rapid and direct method is provided which may be individually adjusted to patients and will entail fewer complications due to an exact determination of the dry weight. It is also of advantage that the ratio between the blood volume and the rebound to the condition of hydration remains unaffected even in the case of changes of the dry weight.

Specific advantageous embodiments of the present invention are stated in the subclaims.

BRIEF DESCRIPTION OF THE DRAWINGS

The invention is best understood from the following detailed description when read in connection with the accompanying drawings. Included in the drawings are the following figures:

FIG. 2 shows a schematic architecture of a neuronal network for use in the present invention;

FIG. 3 shows a table including exemplary results of various cycles of a neuronal network; and FIG. 4 shows another table including exemplary results of various cycles of different neuronal networks having different input levels and hidden levels.

DETAILED DESCRIPTION OF THE PREFERRED EMBODIMENTS

Figure 1:
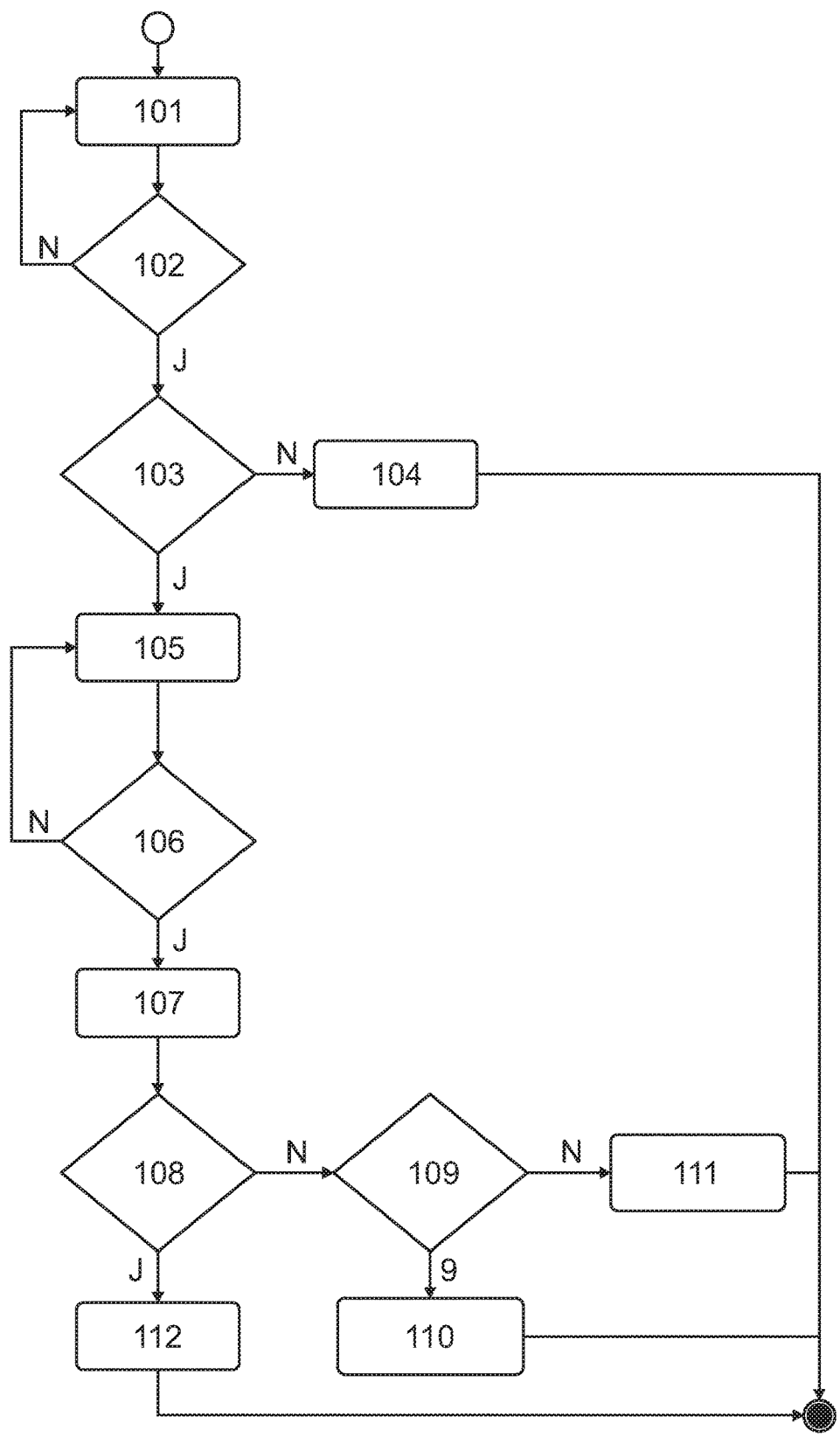
FIG. 1 shows a flow diagram of a method for determining the dry weight according to a first embodiment.

Hereinafter, preferred embodiments of the present invention shall be described by way of the example of an adaptive measuring system for determining/judging the dry weight of a patient.

Accordingly, it is intended to make an as exact statement as possible about the dry weight with the blood volume values collected during and after the dialysis. The blood volume rebound, i.e. the increase in the blood volume after termination of the therapy, is used to make a statement about reaching the dry weight and the degree of a possible hypervolemia or hypovolemia. In general, it is applicable that the higher the increase in the blood volume in the wake of therapy, the higher the degree of hypervolemia of the patient and the higher the still tolerable ultrafiltration volume/the still tolerable ultrafiltration quantity.

By way of a suitable processing of the blood volume values, the increase in the blood volume upon termination of the therapy can be automatically evaluated and an exact statement about reaching the dry weight can be made. For this, the blood volume values after reaching the given/predetermined ultrafiltration value are recorded for a certain period of time and are evaluated with the aid of a learning means (e.g. a neuronal network) based on an algorithm, for example. The learning means then calculates/establishes the still missing or the superfluous ultrafiltration volume so that the physician may appropriately adapt his/her next therapies.

According to the embodiments described hereinafter, a neuronal network is provided as an example of the learning means which evaluates the increase in the rebound so as to determine the required ultrafiltration volume for reaching the dry weight. The neuronal network may be trained, for example, with the aid of data of clinical studies (carried out before) or other predetermined training data. The training thus constitutes a prerequisite for the definition of an established neuronal network for determining or judging the dry weight. For said data in the case of stable dialysis patients having a known dry weight the ultrafiltration is stopped at a particular point in time before the end of therapy at a known remaining ultrafiltration volume and the blood volume rebound is recorded for 15 minutes (e.g. with the help of a hematocrit, toxin, ultrasound or substance concentration sensor which is either integrated in the dialysis machine or external). The pairs of data obtained in this way are transmitted to the network for training. The neuronal network learns from the training which blood volume rebound corresponds to which volume quantity. Following the studies, the trained neuronal network is implemented in the dialysis machine.

FIG. 1 illustrates a flow diagram of a (control) method for determining the dry weight according to a first embodiment. The method may be implemented e.g. as a computer program whose code mediums (instructions etc.) generate the following steps, when the program is run on a computer system.

In step 101 a dialysis therapy including blood volume monitoring is carried out. The therapy parameters (e.g. time of therapy) are adapted so that the required ultrafiltration volume is reached a predetermined period (e.g. 15 min) before the actual end of therapy. In step 102 it is checked whether or not the time of therapy minus the predetermined period has been reached already. When the therapy time minus the predetermined period is reached, the cycle proceeds along the yes branch (J) to step 103. Otherwise, the cycle returns to step 101 along the no branch (N).

In step 103 it is checked whether or not the desired ultrafiltration volume is reached. Unless the ultrafiltration volume is reached, the cycle proceeds along the no branch (N) to step 104 and the therapy is continued until the ultrafiltration volume is reached or is terminated and the excessive volume will be withdrawn during the next therapy.

If it is determined in step 103, on the other hand, that the ultrafiltration volume has been reached, the cycle proceeds along the yes branch (J) to step 105 and the therapy is carried out without any ultrafiltration up to the end of the therapy time. During the residual time of the predetermined period (e.g. 15 min) the blood volume monitoring is continued.

In the following step 106 it is checked whether the therapy time has been reached. If this is not the case, the cycle returns to step 105 along the no branch (N). Otherwise, the cycle proceeds along the yes branch (J) to step 107 where the blood volume values, more exactly speaking the blood volume rebound, are stored for evaluating the dry weight and are evaluated by the neuronal network. After this evaluation, the neuronal network checks in the subsequent step 108 whether the dry weight has been reached. If in step 108 it is determined, based on the empirical values of the neuronal network learnt by training, that the dry weight has not yet been reached, the cycle proceeds along the no branch (N) to step 109 where it is checked whether hypervolemia or hypovolemia of the patient is given. Furthermore, the neuronal network establishes exact information about the volume quantity of the hydration condition. If in step 109 hypervolemia is calculated, the cycle proceeds along the yes branch (J) to step 110 where the patient is automatically continued being ultrafiltrated or a physician (system user) is informed about the hypervolemia.

If, on the other hand, in step 109 hypovolemia is calculated, the cycle proceeds along the no branch (N) to step 111 where e.g. automatically an infusion of a physiologic salt solution is triggered as a bolus or the physician (system user) is informed about the hypovolemia.

If it is determined in step 108 that the dry weight has been reached, the cycle proceeds along the yes branch (J) to step 112 and the process is terminated. The therapy thus can be terminated.

According to the embodiment, a neuronal network that is individual for each patient is provided which can be individually adapted to the patient. According to the same principle of training as afore-mentioned, data pairs of rebound ultrafiltration quantity can be established for the respective patient and can be transmitted to the neuronal network for training. This is only possible, however, when the patient has reached a stable condition already and therefore the dry weight is largely known, as otherwise no statement can be made about the remaining ultrafiltration volume. If this is the case, as in the afore-described studies the ultrafiltration can be stopped from a particular point in time and the blood volume rebound can be recorded until the end of therapy. The pairs of data of the individual patient obtained in this way are input to the system for training so that the neuronal network is continuously capable of furnishing precise statements about the fluid balance of the respective patient.

Another variant for the neuronal network that is individual for each patient is a continuous training for which input information is required from the medical staff. The staff members adjust an ultrafiltration volume and wait for the blood volume rebound at the end of therapy. Before, the system was trained by the data of the clinical studies. The blood volume rebound is evaluated with the aid of said neuronal network and the operator is requested to judge whether the displayed statement is correct. Unless this is the case, the operator is requested to inform the system about the hydration condition of the patient and about his/her possible adaptations to the ultrafiltration volume. Said data are stored again and are made available to another neuronal network, the personal neuronal network, for training. In this way, the personal neuronal network is automatically adjusted to the respective patient over time and with the aid of the operator.

Since moreover even when making use of the network an operator may continue to be requested to check the result, the network can be newly adapted and trained at any time.

The afore-described solutions promise high precision by the individual training data. Even if the weight is varying, the ratio of the blood volume rebound to the hydration condition remains unaffected.

Hereinafter the applicability of the embodiments shall be discussed in detail. For this purpose, a neuronal network was chosen which evaluates blood volume values and, on the basis thereof, calculates the dry weight.

FIG. 2 illustrates a schematic architecture of a neuronal network for use in the embodiments.

A neuronal network may be implemented as a software solution which is applied for identifying patterns and courses, for fitting curves and for further problems. It consists of an input layer 201 which may contain any number of input parameters 20. This layer is followed by one or more hidden layers 202 which are linked to each other via different activating functions (e.g. sigmoid function). Each hidden layer 202 may have a variable number of neurons 23. Finally, the last hidden layer 202 leads to the output layer 203 which outputs one or more output parameters 24. It is important to mention that, depending on the selected number of hidden layers 202 and neurons 23, the expected results and the capability of the network may strongly vary (which can be determined with the aid of the mean square error (MSE) between the calculated output and the actual output). With a large number of layers and neurons, respectively, overfitting may easily occur, whereas a low number does not offer sufficient space for exactly weighting the output.

Each neuronal network passes two steps: training and validation. For the training, there are different training algorithms such as e.g. the back-propagation process, which shall not be discussed in detail here, however. In the training known input-output pairs are transmitted to the network. The network attempts to achieve the expected output via the different activating functions to which the neurons are linked. Accordingly, the neuronal network weights the different connections 22 between the neurons 23 of the different layers in a differently strong way, until a certain error tolerance or a maximum number of training cycles has been reached. Validation is performed after the training in that again known input-output pairs are transmitted to the network and the latter compares the correct outputs to the ones calculated by itself.

With an approach validation with the aid of therapy data a neuronal network was drafted, trained and validated with the help of 48 therapy data. Said therapy data comprised blood volume, ultrafiltration and blood pressure values of anonymous dialysis patients. For the training, the neuronal network requires blood volume rebound values that are missing in the therapy data. For this reason, the blood volume rebound was processed from the individual therapy data as follows.

Changes in the blood volume mainly occur from the difference of ultrafiltration and refilling. This simplified consideration allows to calculate the refilling back on the basis of the blood volume and ultrafiltration data of the therapies. The calculation shall not be discussed here in detail, however. The refilling calculated in this way then was adapted (fitted) to the desired period of time after therapy taking the blood volume rebound behavior known from literature into account. With the aid of the fitted refilling curves the blood volume rebounds then could be calculated.

The training was carried out with 30 out of 48 of the afore-mentioned therapy data. In the following, the best possible network parameters were determined for evaluation of the processed blood volume rebounds. For this purpose, the input parameters were transmitted to different network configurations, were trained and validated. In so doing, three different respective input parameters (blood volume rebound, blood volume rebound plus the last blood volume value of the therapy, blood volume values of the complete therapy) are encountering one to three respective hidden layers each having three to ten neurons. Each configuration was trained ten times. After completing the training cycle, the neuronal network with the best performance out of 11970 individual trainings, for example, was obtained.

For the processed therapy data, a total of six of the afore-described training cycles were run so that a total of 71820 individual trainings took place.

FIG. 3 illustrates a table including exemplary results of the best outputs of different cycles of a neuronal network.

Accordingly, it is evident that five of the six cycles encountered the blood volume rebound as input parameter and three hidden layers, wherein only one cycle achieved the best performance with a blood volume rebound and the last blood volume value as input parameter. This cycle also had shown the best output of 27.5 ml$^2$. It is clearly evident, however, that also the neuronal networks with an output of 30.6 ml$^2$ to 41.5 ml$^2$ furnished very good results. Thus, the difference of the performance (not shown in FIG. 3) in the neuronal network with the worst output of 41.5 ml$^2$ is higher by only 1 ml than in the network with the best output of 27.5 ml$^2$. For this reason, only the blood volume rebound can be incorporated in the neuronal network as input parameter.

FIG. 4 shows another table including exemplary results of different cycles of various neuronal networks having different input levels and hidden levels.

A first neuronal network 1 with a blood volume rebound as input parameter and three hidden layers, a fourth neuronal network 4 with a blood volume rebound as input parameter and three hidden layers, a fifth neuronal network 5 with a blood volume rebound and the last blood volume value as input parameter and three hidden layers, and a sixth neuronal network 6 with a blood volume rebound as input parameter and three hidden layers furnish the neuronal network having the best performance, wherein a second neuronal network 2 with a blood volume rebound as input parameter and one hidden layer and a third neuronal network 3 with blood volume values of the entire therapy as input parameter and three hidden layers provide an example of a neuronal network of poor performance. The representation of the results of the second neuronal network 2 and of the third neuronal network 3 serve for illustration of the fact that a neuronal network with a certain number of hidden layers and input parameters need not always show good performance.

For implementing the afore-mentioned invention, at the beginning patients' data are necessary. These data can be collected from different dialysis centers and can be processed within the scope of a clinical study (carried out before). Within the scope of said study, stable patients having a known dry weight are involved. With said patients the therapy is stopped, before the end of therapy, at a known residual amount of ultrafiltration volume and the blood volume rebound is recorded over a particular period of time. If possible, also data are detected in which the ultrafiltration volume is even increased in a defined manner.

In this way, various cases of hypervolemia and hypovolemia may be incorporated in the trainings data and the network training will be capable of furnishing better results even for extreme cases. The data obtained in this way (blood volume rebound and ultrafiltration volume) now are transmitted to a neuronal network, the main network.

These results then form the basis of determining the dry weight with the aid of neuronal networks.

Summing up, a system/an apparatus and a (control) method for determining the dry weight of a patient after a dialysis therapy are described, with the blood volume of the patient being monitored and blood volume values being output. The blood volume values are recorded and evaluated for a predetermined period of time after reaching an ultrafiltration volume appropriately predetermined for the patient, wherein the dry weight of the patient is then determined on the basis of the rate of change of the blood volume during a predetermined period of time.

The invention claimed is:

1. A method for evaluating dry weight of a patient after ultrafiltration in a dialysis therapy, comprising the steps of:
 recording blood volume values for a predetermined period of time after reaching an ultrafiltration volume predetermined for the patient in the dialysis therapy;
 evaluating whether the dry weight of the patient is reached, is high, or is low by applying a neuronal network to the recorded blood volume values, the neuronal network trained with known input-output pairs being blood volume rebound values and remaining ultrafiltration blood volume values, respectively; and adapting a subsequent dialysis therapy for the patient based on the dry weight evaluation using the recorded blood volume values.

2. The method of claim 1, further comprising the steps of:
calculating hypervolemia or hypovolemia of the patient based on the recorded blood volume values; and
continuing the dialysis therapy with ultrafiltration when hypervolemia of the patient is calculated and infusing a physiologic salt solution as a bolus when hypovolemia of the patient is calculated.

3. A computer program comprising code mediums for generating the steps according to claim 1 when said program is run on a computer system.

4. The method of claim 1, further comprising the step of training the learning means on the basis of data pairs from the rate of change of blood volume and the ultrafiltration volume of other patients.

5. The method of claim 1, further comprising the step of initiating termination of the dialysis therapy after expiry of a predetermined therapy duration.

6. The method of claim 1, further comprising the step of initiating continuation of the dialysis therapy without ultrafiltration until expiry of a predetermined therapy duration if a predefined dry weight has been reached before expiry of the predetermined therapy duration.

7. The method of claim 1, further comprising the step of establishing information about a hydration condition of the patient based on the blood volume values.

8. The method of claim 1, further comprising the step of continuing dialysis therapy with ultrafiltration if hypervolemia of the patient is calculated.

9. The method of claim 1, further comprising the step of terminating the dialysis therapy when a predefined dry weight for the patient is reached.

10. The method of claim 1, further comprising:
checking at a predetermined time period before the end of a therapy is reached whether the desired ultrafiltration volume is reached,
until the ultrafiltration is reached:
carrying out the therapy with ultrafiltration if the desired ultrafiltration volume is not reached,
carrying out the therapy without ultrafiltration if the desired ultrafiltration volume is reached; and
storing blood volume values at the end of the therapy to record blood volume values evaluated to determine the dry weight.

\* \* \* \* \*